(12) United States Patent
Fuchigami et al.

(10) Patent No.: US 10,189,054 B2
(45) Date of Patent: Jan. 29, 2019

(54) DEVIATION HANDLING APPARATUS AND DEVIATION HANDLING METHOD

(71) Applicant: Freund Corporation, Tokyo (JP)

(72) Inventors: Shouji Fuchigami, Tokyo (JP); Shigemi Isobe, Tokyo (JP); Norikazu Saitou, Tokyo (JP); Takashi Terada, Tokyo (JP)

(73) Assignee: Freund Corporation, Tokyo (JP)

( * ) Notice: Subject to any disclaimer, the term of this patent is extended or adjusted under 35 U.S.C. 154(b) by 0 days.

(21) Appl. No.: 15/686,723

(22) Filed: Aug. 25, 2017

(65) Prior Publication Data

US 2018/0056332 A1    Mar. 1, 2018

(30) Foreign Application Priority Data

Aug. 31, 2016 (JP) .................................. 2016-169956

(51) Int. Cl.
| | | |
|---|---|---|
| *B65G 53/40* | (2006.01) | |
| *B07B 13/16* | (2006.01) | |
| *G01N 33/15* | (2006.01) | |
| *B07C 5/342* | (2006.01) | |
| *B65G 53/56* | (2006.01) | |

(52) U.S. Cl.
CPC .............. *B07B 13/16* (2013.01); *B07C 5/342* (2013.01); *B65G 53/40* (2013.01); *B65G 53/56* (2013.01); *G01N 33/15* (2013.01)

(58) Field of Classification Search
CPC ........................... B65G 53/4691; B65G 53/40
USPC ................................. 406/181, 182, 183, 169
See application file for complete search history.

(56) References Cited

U.S. PATENT DOCUMENTS

| | | | | | |
|---|---|---|---|---|---|
| 3,232,494 | A | * | 2/1966 | Poarch .................... | F16K 3/06 137/575 |
| 3,966,048 | A | * | 6/1976 | Nunes ..................... | B07C 5/04 198/340 |
| 4,127,478 | A | * | 11/1978 | Miller ..................... | B03B 5/56 209/240 |

(Continued)

FOREIGN PATENT DOCUMENTS

| | | |
|---|---|---|
| JP | 2008-183168 | 8/2008 |
| JP | 2012-525895 | 10/2012 |
| WO | 2009/130539 | 10/2009 |

*Primary Examiner* — Joseph A Dillon, Jr.
(74) *Attorney, Agent, or Firm* — Wenderoth, Lind & Ponack, L.L.P.

(57) ABSTRACT

A deviation handling apparatus for a continuous production system of granulated products includes a storage section for temporarily storing the products, an inspection section for inspecting selected physical properties of the products, a moving route switching section for switching the moving route of the products according to the results of the inspection and a discharge path for discharging the products judged as not meeting the specifications. The storage section has two shutoff valves and a storage chamber formed therebetween. The switching section has a switching valve having a normal position and a deviation position for causing a conveyance route to communicate with the discharge path. The deviation handling apparatus closes the shutoff valves to store products in the storage chamber and inspect properties of the products. When off-specification products are detected, the switching valve is switched to the deviation position and the products are discharged.

5 Claims, 3 Drawing Sheets

(56) References Cited

U.S. PATENT DOCUMENTS

| | | | | |
|---|---|---|---|---|
| 4,193,502 A * | 3/1980 | Marmo | B07C 5/36 | |
| | | | 209/555 | |
| 4,222,488 A * | 9/1980 | Jones | B07C 5/3412 | |
| | | | 209/583 | |
| 4,448,678 A * | 5/1984 | Gentry | B03B 1/00 | |
| | | | 209/3 | |
| 4,570,783 A * | 2/1986 | Newcom | B65G 47/5113 | |
| | | | 198/347.1 | |
| 4,631,125 A * | 12/1986 | Parks | B01F 13/10 | |
| | | | 198/560 | |
| 4,756,427 A * | 7/1988 | Gohde | G01N 15/1404 | |
| | | | 209/3.1 | |
| 4,832,700 A * | 5/1989 | Kaspar | B01J 2/16 | |
| | | | 209/138 | |
| 4,863,040 A * | 9/1989 | Sandi | B07C 5/344 | |
| | | | 193/31 A | |
| 4,995,765 A * | 2/1991 | Tokuhiro | B65F 5/005 | |
| | | | 209/580 | |
| 5,238,496 A * | 8/1993 | Koponen | B05B 13/0221 | |
| | | | 118/324 | |
| 5,368,731 A * | 11/1994 | Pesotini | B01D 29/01 | |
| | | | 162/240 | |
| 5,507,947 A * | 4/1996 | Kriegl | B01D 33/11 | |
| | | | 210/161 | |
| 5,698,109 A * | 12/1997 | Payne | C02F 1/5227 | |
| | | | 209/5 | |
| 6,000,645 A * | 12/1999 | Preisser | B03B 9/063 | |
| | | | 241/41 | |
| 6,068,428 A * | 5/2000 | Nair | B65G 51/01 | |
| | | | 406/109 | |
| 6,325,311 B1 * | 12/2001 | Preisser | B03B 9/063 | |
| | | | 241/299 | |
| 7,905,357 B2 * | 3/2011 | Svatek | B07C 5/34 | |
| | | | 209/246 | |
| 8,641,329 B2 * | 2/2014 | Barrios | B65G 51/14 | |
| | | | 137/875 | |
| 2003/0194281 A1 * | 10/2003 | McKinnis | A01H 4/001 | |
| | | | 406/181 | |
| 2008/0251431 A1 * | 10/2008 | Fioratti | C04B 26/18 | |
| | | | 209/646 | |
| 2015/0298919 A1 * | 10/2015 | Le | B65G 51/32 | |
| | | | 406/110 | |

\* cited by examiner

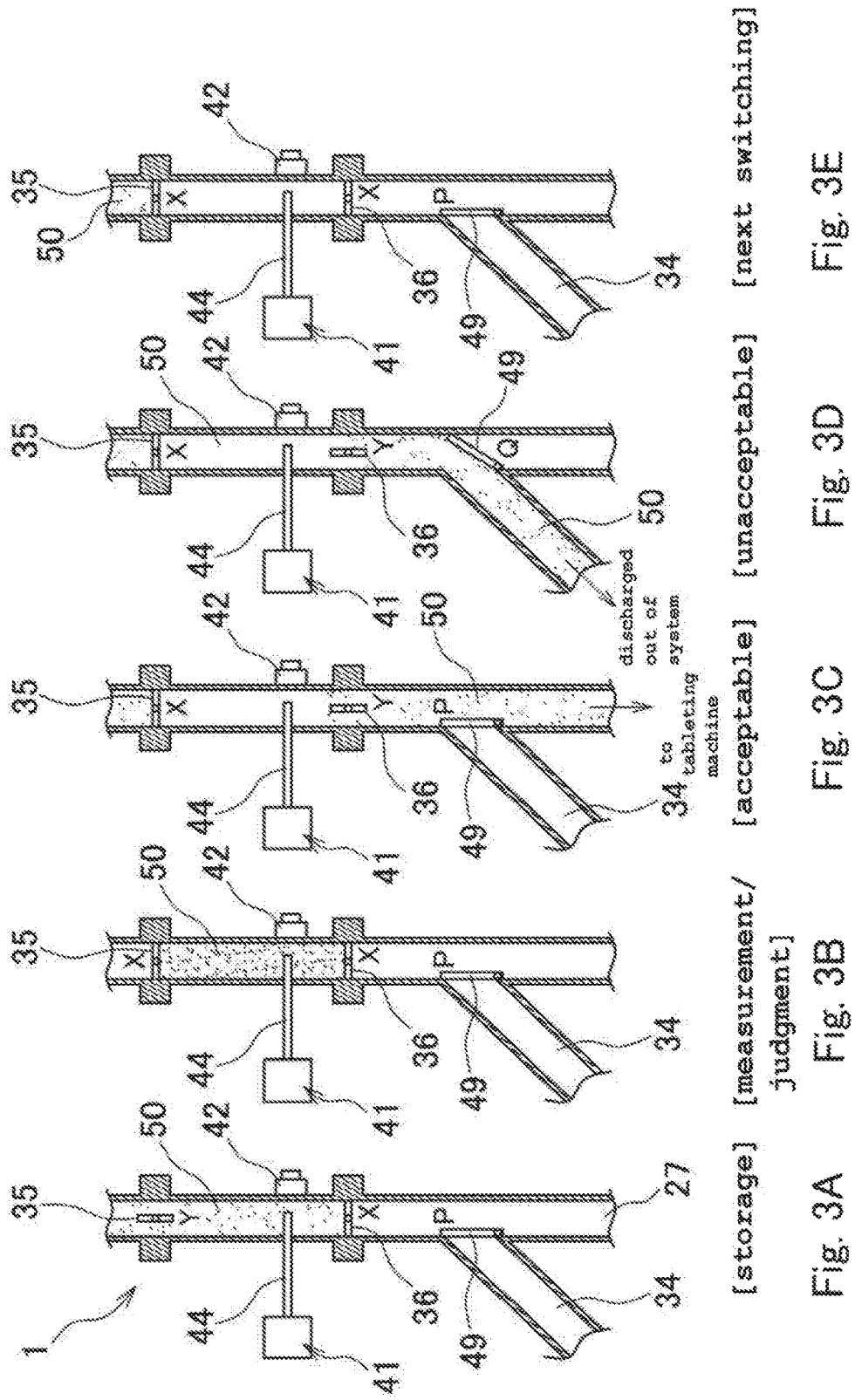

DEVIATION HANDLING APPARATUS AND DEVIATION HANDLING METHOD

BACKGROUND OF THE INVENTION

Field of the Invention

This invention generally relates to the technological field of quality control for continuous production systems of pharmaceutical products etc. More particularly, the present invention relates to detection/deviation handling of off-specification products.

Related Art Statement

In the field of manufacturing of pharmaceutical products, a sampling inspection is executed on a batch by batch basis to measure some of the physical properties of the products and check the quality of the products because a certain level of quality needs to be secured for the products. With such batch inspections, once a sampled product is determined as off-specification, all the products of the batch are disposed as waste to entail a large loss in terms of both the number of products and manufacturing cost. Particularly, when mass production is involved, the magnitude of production becomes huge and the batch size also becomes large to give rise to a serious problem of a large loss once an off-specification product is detected in a batch.

Meanwhile, research efforts have been paid and continuous production systems have been developed in recent years for the purpose of achieving high production efficiency. However, since products are manufactured continuously in a continuous production system, the notion of "a batch" can hardly apply to such a system. Consequently, when an off-specification product is detected in a continuous production process and all the products produced from the entire production process are regarded as a batch of products, all the products need to be disposed as waste to consequently entail a huge loss. For this reason, with continuous production systems, the products are constantly observed or periodically observed at predetermined time intervals so as not to produce an off-specification product and the production conditions are controlled by a feedback control system.

However, if a feedback control system is in place, off-specification products can inevitably appear once an abnormal situation arises for the system. Additionally, the production conditions may not be stable immediately after the start and/or before the end of a production process to make it difficult to secure a stable production of specifications-satisfying products. On the other hand, conventional production systems normally do not have a mechanism or a site for discharging off-specification products out of the production system. Therefore, if an off-specification product is produced while a production line is in operation, the production line needs to be suspended at worst. Furthermore, when an off-specification product is detected, it may be possible to remove some products that precede and succeed the off-specification product from the production line. However, since products are constantly moving, it is difficult to determine the range of products to be removed from the production line. Additionally, if an off-specification product is detected, it may already have been moved away far downstream so that a relatively large number of products that precede and succeed the off-specification product may have to be removed from the production line from the viewpoint of reliability. Then, there arises a problem that the loss of products will inevitably be large.

SUMMARY OF THE INVENTION

Thus, the present invention relates to a deviation handling apparatus and a deviation handling method.

A deviation handling apparatus according to the present invention is to be used for a continuous production system of granulated products. It is designed to discharge granulated products that do not meet predetermined product specifications out of the system.

The deviation handling apparatus according to the present invention comprises: a storage section, an inspection section, a discharge path and a switching section. The storage section temporarily stores granulated products. The inspection section inspects selected physical properties of the granulated products, such as the particle size distribution, the average particle size, the uniformity of the ingredients content, the content of specific ingredients, the amount of moisture, in the storage section. The discharge path is arranged downstream relative to the storage section to discharge the granulated products to the outside of the continuous production system. The switching section switches the moving route of the granulated products according to the result of the inspection by the inspection section so as to guide the granulated products judged as not meeting the specifications to the discharge path.

According to the present invention, a deviation handling apparatus having a storage section for temporarily storing granulated products is arranged in a continuous production system of granulated products. The deviation handling apparatus additionally has an inspection section and a switching section, of which the inspection section measures selected physical properties of the granulated products in the storage section. When off-specification products are detected as a result of the measurement, the switching section switches the moving route of granulated products and the granulated products that are judged as not meeting the specifications are guided to a discharge path and discharged from the system. With this arrangement, selected physical properties of granulated products are measured on a small unit basis so as to reliably discharge off-specification products from the system but limit the amount of off-specification products to be discharged from the system at a time.

Meanwhile, a deviation handling method according to the present invention is also to be used for a continuous production system of granulated products. It is designed to discharge the granulated products that do not meet predetermined specifications from the system.

The deviation handling method according to the present invention comprises: temporarily storing the granulated products; inspecting selected physical properties of the stored granulated products; and discharging the granulated products judged as not meeting the specifications as a result of the inspection from the system.

Thus, according to the present invention, when some granulated products are judged as not meeting predetermined specifications as a result of a measurement, those granulated products that are judged as not meeting the specifications are discharged from the system. With this arrangement, selected physical properties of granulated products are measured on a small unit basis so as to reliably discharge off-specification products from the system but limit the amount of off-specification products to be discharged from the system at a time.

Thus, a deviation handling apparatus and a deviation handling method according to the present invention can reliably eliminate off-specification products from a continuous production system and secure a predetermined quality level for the system. Additionally, since selected physical properties of granulated products are measured on a small unit basis so that the amount of off-specification products to be discharged from the system at a time is limited and the manufacturing loss is minimized.

BRIEF DESCRIPTION OF THE DRAWINGS

FIGS. 3A-3E are explanatory drawings of the sequence of inspection/deviation handling operations for granulated products in a deviation handling apparatus according to the present invention.

DESCRIPTION OF THE PREFERRED EMBODIMENT

Figure 1:
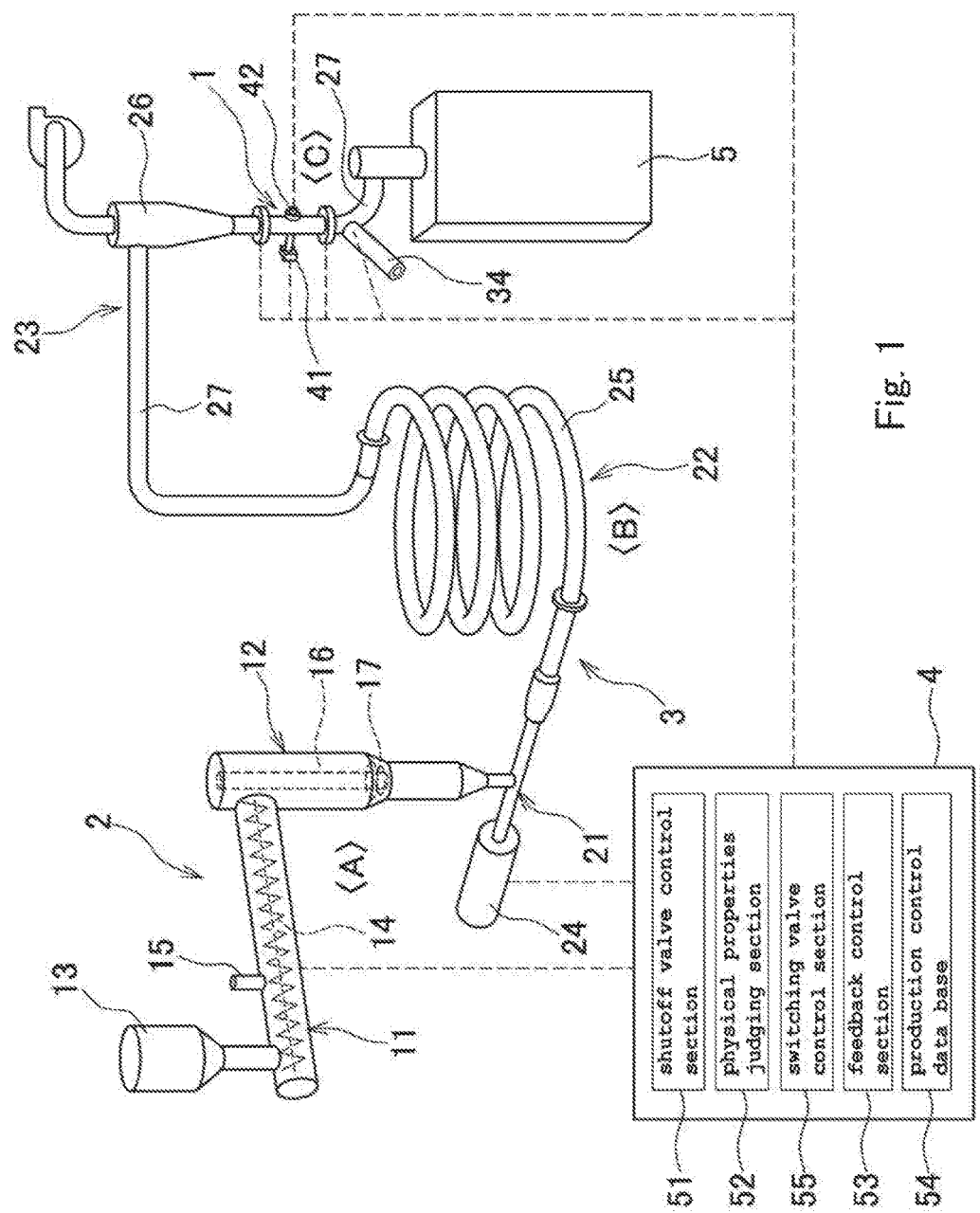
FIG. 1 is an explanatory drawing showing a schematic configuration of a continuous production system of granulated products that is provided with an embodiment of deviation handling apparatus according to the present invention.

Hereinafter, an embodiment of the present invention will be described. The object of the present embodiment is to provide a deviation handling apparatus and a deviation handling method that can reliably eliminate off-specification products and minimize the number of off-specification products to be eliminated, in a continuous production system for pharmaceutical products. FIG. 1 is an explanatory drawing showing a schematic configuration of a continuous production system of granulated products that is provided with an embodiment of a deviation handling apparatus 1 according to the present invention. Referring to FIG. 1, the continuous production system of granulated products is designed to execute wet granulation step A, using a continuous granulation apparatus 2, drying step B, using a spiral drying apparatus 3 and inspection/deviation handling step C, using the deviation handling apparatus 1 according to the present invention and the system is controlled by a system control unit 4. The granulated products produced from this system are, if necessary, appropriately subjected to a sizing step, a sieving step and/or a lubricant-mixing step and subsequently transferred to a tableting machine 5, where they are turned into tablets. The tablets produced from the tableting machine 5 are then, if necessary, appropriately subjected to a coating process and produced as finished products.

In the wet granulation step A, wet and granulated products are formed by means of the continuous granulation apparatus 2. The continuous granulation apparatus 2 comprises a mixing/kneading/granulation section 11 and a size regulating section 12. The mixing/kneading/granulation section 11 operates for continuous mixing/kneading/granulation to produce wet granulated products. The size regulating section 12 operates for continuously sizing the wet granulated products produced from the mixing/kneading/granulation section 11 so as to make them show an intended particle size. A source mixture for producing granulated products is supplied to the mixing/kneading/granulation section 11 from a source material supply vessel 13 and mixed and kneaded by means of a screw 14 to produce wet granulated products. For this operation, water and binding solution are appropriately added to the powdery source material from a solution supply section 15. The wet granulated products formed by the mixing/kneading/granulation section 11 are then fed to a sizing chamber 16 in the size regulating section 12. The wet granulated products are then crushed by an impeller 17 arranged in the sizing chamber 16 and fed to the downstream drying apparatus 3.

The drying apparatus 3 of the drying step B comprises a granulated products infeed section 21, a drying treatment section 22 and a product collecting section 23. Wet granulated products are fed into the granulated products infeed section 21 from the continuous granulation apparatus 2 and, at the same time, hot high pressure air is fed into the granulated products infeed section 21 from a hot air supply apparatus 24. The drying treatment section 22 comprises a looped pipe 25 wound along a horizontal direction. As shown in FIG. 1, the looped pipe 25 has a configuration that a pipe wound three steps (windings) is laterally installed in a horizontal direction. The product collecting section 23 is arranged downstream relative to the drying treatment section 22 and comprises a cyclone collector 26.

The wet granulated products produced from the continuous granulation apparatus 2 are then supplied to the granulated products infeed section 21. The supplied wet granulated products are then introduced into the looped pipe 25 along with the hot air supplied from the hot air supply apparatus 24 and dried there by hot air as they are blown to flow through the looped pipe 25. The dried granulated products are then discharged from the looped pipe 25 with hot air and collected by the cyclone collector 26.

Figure 2:
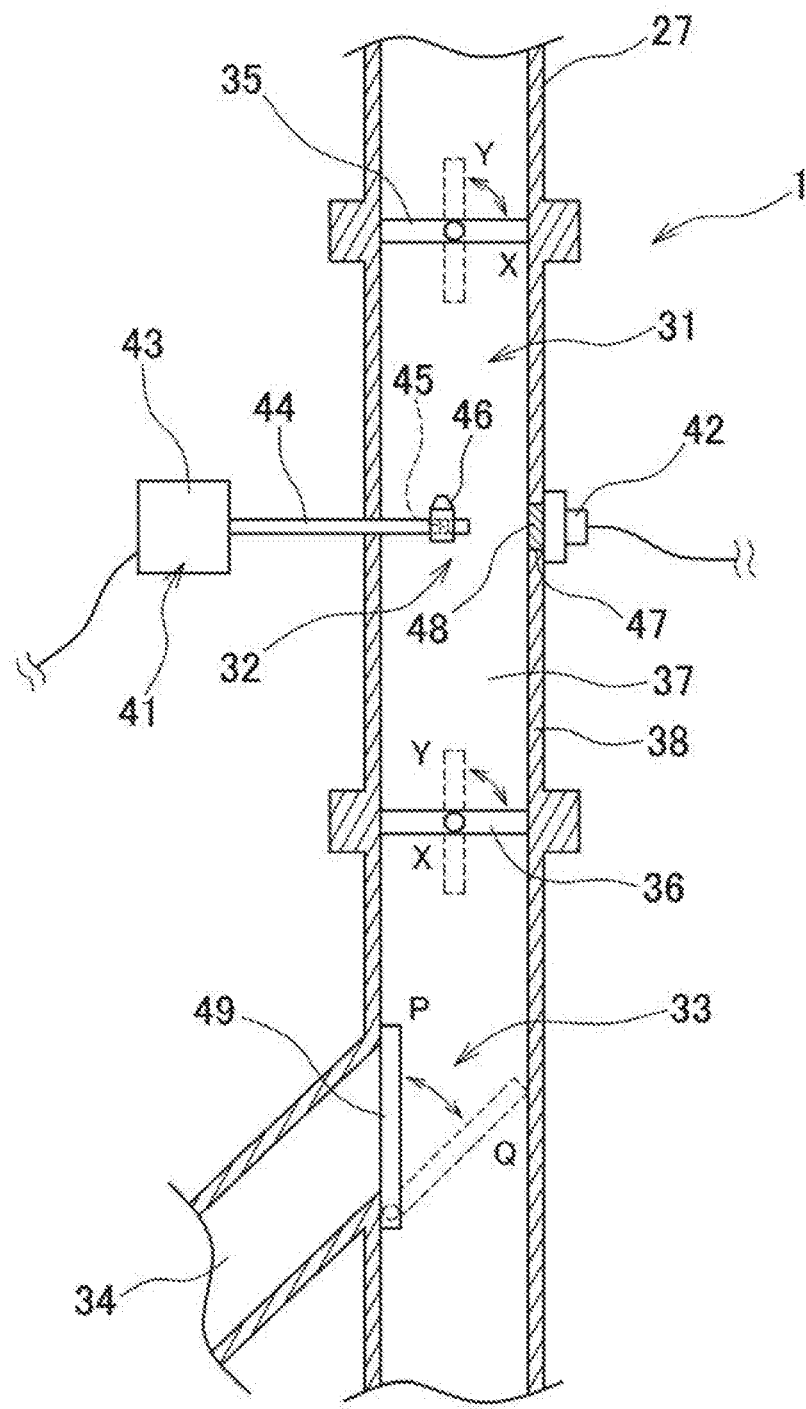
FIG. 2 is an explanatory drawing of the deviation handling apparatus used in the control system of FIG. 1, showing the configuration thereof.

A deviation handling apparatus 1 is arranged for the inspection/deviation handling step C. FIG. 2 is an explanatory drawing of the deviation handling apparatus 1, showing the configuration thereof. In this system, the deviation handling apparatus 1 is arranged at the conveyance route 27 between the cyclone collector 26 and the tableting machine 5. As shown in FIG. 2, the deviation handling apparatus 1 comprises a storage section 31, an inspection section 32, a moving route switching section 33 and a discharge path 34. The storage section 31 temporarily stores the granulated products fed from the drying step B. The inspection section 32 inspects selected physical properties of the granulated products in the storage section 31. The switching section 33 switches the moving route of the granulated products according to the result of the inspection by the inspection section 32. The discharge path 34 is employed to discharge granulated products that are judged as off-specification products by the inspection section 32 to the outside of the system.

The storage section 31 has two shutoff valves 35 (the first valve) and 36 (the second valve) arranged respectively at the upstream side and at the downstream side. Pneumatically actuated butterfly valves are typically employed for the shutoff valves 35 and 36, each of which has a closed position X and an open position Y. The operations of the valves 35 and 36 are controlled by shutoff valve control section 51 of the control unit 4. As the shutoff valves 35 and 36 are made to take the respective closed positions X, the conveyance route 27 is closed and a hermetically sealed storage chamber 37 is produced in the storage section 31. In this system, the storage chamber 37 is made to have a relatively small size, whose capacity is approximately 1 L. When the downstream side valve 36 is closed while a granulation process is being executed, the granulated products that are flowing into the storage section 31 by way of the conveyance route 27 are blocked and held there. Thereafter, as the upstream side valve 35 is closed, the granulated products that have flown into the storage chamber 37 after the closure of the downstream side valve 36 are stored in the storage chamber 37 in a hermetically sealed condition.

The inspection section 32 measures the critical material attribute (CMA) of the granulated products. The deviation handling apparatus 1 is provided with two physical property detecting means arranged along the lateral wall 38 of the storage chamber 37 for the inspection section 32. The two physical property detecting means of this system include a laser particle size distribution measuring instrument 41 and a near infrared sensor (to be referred to as NIR sensor hereinafter) 42. Both the particle size distribution measuring instrument 41 and the NIR sensor 42 are also controlled by the control unit 4. The data obtained by the measuring instrument 41 and the sensor 42 are sent out to a physical properties judging section 52 of the control unit 4. The physical properties data obtained by the inspection section 32 are also sent to a feedback control section 53 of the control unit 4 and employed for feedback control of the continuous granulation apparatus 2 and the drying apparatus 3. The physical properties data are associated with UTC (coordinated universal time) and recorded in a production control data base 54 to secure traceability of the data.

The laser particle size distribution measuring instrument 41 comprises a measurement unit 43 and a probe 44. The probe 44 is provided with a groove-shaped measurement zone 45 formed at the front end of the probe 44. The measurement zone 45 is irradiated with a laser beam so that the particle size distribution and the average particle size of the granulated products in the measurement zone 45 can be measured. The probe 44 is arranged in such a way that it partly projects into the storage chamber 37 from the lateral wall 38 and the measurement zone 45 is located in the storage chamber 37. A dispersion unit 46 is fitted to the front end of the probe 44 in order to improve the accuracy of measurement of particle sizes. The dispersion unit 46 introduces granulated products into the measurement zone 45 in a dispersed manner so as to reduce the density of the granulated products that are being introduced into the measurement zone 45. The inspection section 32 irradiates the granulated products that have flown into the measurement zone 45 of the measuring instrument 41 with a laser beam and detects the particle size distribution and the average particle size thereof on a real time basis.

The NIR sensor 42 is a type of optical sensor that irradiates rays (near infrared rays: wavelength of about 800 to 3,000 nm) for inspection onto the granulated products in the storage chamber 37. Thanks to the provision of the sensor 42, selected physical properties (including the uniformity of the ingredients content, the content of specific ingredients, the amount of moisture) can be detected in a non-contact and non-destructive manner. A through hole 47 is bored through the lateral wall 38 and a piece of transparent tempered glass 48 is fitted to the through hole 47. The sensor 42 is so arranged as to face the inside of the storage chamber 37 by way of the piece of tempered glass 48 such that the NIR rays emitted from the sensor 42 may reach the inside of the storage chamber 37. Thus, in the inspection section 32, the sensor 42 irradiates the granulated products in the storage chamber 37 with near infrared rays and determines physical properties of the granulated products such as the amount of moisture thereof by calculations using optical characteristic values of the granulated products such as the absorbance.

The moving route switching section 33 is equipped with a switching valve 49 for switching the conveyance route of granulated products. A pneumatically driven damper is typically employed for the switching valve 49. It has a normal position P (the first position) and a deviation position Q (the second position). The operation of the valve 49 is controlled by switching the valve control section 55 of the control unit 4. When the valve 49 is at the normal position P, the conveyance route 27 is in communication with the tableting machine 5. When, on the other hand, the valve 49 is at the deviation position Q, the conveyance route 27 is shut off from the tableting machine 5 but brought into communication with the discharge path 34. The valve 49 ordinarily takes the normal position P but once an off-specification product is detected by the inspection section 32, its position is switched to the deviation position Q. Thus, as the valve 49 is actuated, the moving route of the granulated products in the storage chamber 37 is switched. The granulated products in the storage chamber 37 are sent to the tableting machine 5 as long as they are determined as acceptable as a result of an inspection by the inspection section 32 but sent to the discharge path 34 once an off-specification product is detected and determined as unacceptable by the inspection section 32.

The deviation handling apparatus 1 executes a deviation handling process on off-specification products (rejected products) in a manner as described below. FIG. 3 is an explanatory drawing of the sequence of inspection/deviation handling operations for granulated products in the deviation handling apparatus 1. The deviation handling apparatus 1 executes the sequence of operations as shown in FIG. 3 under the control of the control unit 4. Firstly, as shown in FIG. 3A, the apparatus 1 closes the downstream shutoff valve 36 by means of the shutoff valve control section 51 (shutoff position X). As the valve 36 is closed, the granulated products 50 flowing through the conveyance route 27 are blocked and start to be stored in the storage section 31. Subsequently, when a predetermined period of time has elapsed (e.g., about 1 min.), the apparatus 1 closes the upstream side shutoff valve 35 as shown in FIG. 3B (shutoff position X). As the valve 35 is closed, a storage chamber 37 having a capacity of about 1 L is produced in the storage section 31 and hence about 1 L of granulated products 50 that have undergone a drying process are stored in the storage chamber 37 in a hermetically sealed condition.

Then, in the state where the granulated products 50 are stored in the storage chamber 37, selected physical properties of the granulated products 50 are measured by the inspection section 32. More specifically, the deviation handling apparatus 1 executes a CMA measurement operation on a relatively small group of products. For this CMA measurement operation, as described above, the deviation handling apparatus 1 closes not only the downstream valve 36 but also the upstream valve 35 defining the storage section 31 to produce a hermetically sealed storage chamber 37. Therefore, no air flows from upstream into the storage chamber 37 to unnecessarily stir the granulated products 50 in the storage chamber 37 so that the apparatus 1 can measure the selected physical properties of the granulated products on a stable basis. As pointed out above, in this embodiment, the particle size distribution measurement instrument 41 measures the particle size distribution and the average particle size of the granulated products 50 and the NIR sensor 42 measures the amount of moisture of the granulated products 50.

The results of the measurements obtained by the measurement instrument 41 and the sensor 42 are transmitted to the control unit 4. The physical properties judging section 52 of the control unit 4 makes a judgment for acceptableness or unacceptableness on the basis of the numerical values of the results of measurements that have been transmitted to it. More specifically, when each of the physical property values are within a specified range (between upper and lower threshold values), the physical properties judging section 52 judges that the granulated products 50 in the storage chamber 37 are specifications-meeting products (acceptable products). When the granulated products are judged as acceptable, the control unit 4 causes the shutoff valve control section 51 to open the valve 36 (open position Y) in a state where the switching valve 49 is held to the ordinary position P. Then, as a result, the granulated products 50 that have been judged as acceptable flow out from the storage chamber 37 and are sent to the tableting machine 5 by way of the conveyance route 27 (in FIG. 3C).

When, on the other hand, one or more than one of the physical property values of the granulated products are determined to be out of the specified range, the physical properties judging section 52 judges that the granulated products 50 are off-specification products (unacceptable). Then, the control unit 4 firstly shifts the valve 49 to the deviation position Q by means of the switching valve control section 55. More specifically, it closes the conveyance route 27 at the side of the tableting machine 5 and opens the discharge path 34. Thereafter, the control unit 4 opens the valve 36 by means of the shutoff valve control section 51. Then, as a result, the granulated products 50 that include off-specification products are guided to the discharge path 34 and the whole lot in the storage chamber 37 is discharged to the outside of the system through the discharge path 34 (in FIG. 3D).

After the operations shown in FIGS. 3A to 3D are executed and all the granulated products 50 in the storage chamber 37 are sent out (in FIG. 3E), the control unit 4 opens the upstream valve 35 and repeats the execution of the operations of those steps. The deviation handling apparatus 1 executes the sequence of operations shown in FIG. 3 in every one minute (in the instance of handling 30 kg/h) so that it measures the selected physical properties and records the obtained physical property data each time. Additionally, the control unit 4 operates for feedback control of the continuous granulation apparatus 2 and the drying apparatus 3 based on the obtained data and appropriately adjusts the number of revolutions per unit time of the screw 14, the water adding rate by the solution supply section 15 and the flow rate and the temperature of the hot air coming from the hot air supply apparatus 24 among others.

As described above, the deviation handling apparatus 1 according to the present invention can measure selected physical properties of granulated products in the continuous production system and at the same time, when it detects an off-specification product as a result of the measurement, discharges the lot including the off-specification product out of the system. Thus, with the above described arrangement, the deviation handling apparatus 1 according to the present invention can reliably eliminate off-specification products from the continuous production system so that it can secure a high quality level of products for the system. Additionally, since it executes micro batch processing operations of measuring selected physical properties of products on a small unit basis, it can minimize the amount of off-specification products to be discharged from the system and hence it can also minimize the loss of products. Furthermore, since it does not discard granulated products produced even immediately after the start or immediately before the end of a production cycle setting a prescribed time period but it conducts deviation handling operations on the basis of the values obtained by actual measurements, it is possible to produce granulated products continuously and effectively without giving rise to any unnecessary waste.

Note that the scope of the present invention is by no means limited by the above described embodiment, which can be modified or altered in various different ways without departing from the spirit of the present invention.

While the deviation handling apparatus 1 is arranged between the cyclone collector 26 and the tableting machine 5 in the above described embodiment, the position of installation of a deviation handling apparatus 1 according to the present invention is not limited to the above described one and may alternatively be arranged between an impeller 17 and a granulated products infeed section 21. While a deviation handling apparatus 1 according to the present invention is preferably arranged at a vertically extending conveyance route because gravity can be utilized to convey granulated products, it can alternatively be arranged at a horizontally extending conveyance route.

The operation of measuring selected physical properties of granulated products may be conducted on each of the manufacturing steps of mixing, granulation, drying and so on, although an additional measuring instrument is required each time a measuring spot is added to entail an increased manufacturing cost. If selected physical properties are measured at a position where granulated products are brought in before they are dried and hence they are still in a wet state, some of the granulated products may adhere to surrounding objects because the granulated products are temporarily held stationary at that position in a deviation handling apparatus 1. For this reason, a deviation handling apparatus 1 such as shown in FIG. 1 is desirably arranged downstream relative to a drying apparatus 3 so that the selected physical properties of the granulated products may be collectively measured after they are dried.

While the capacity of the storage section 31 is made to be equal to about 1 L in the above described embodiment, the capacity of 1 L is shown only as a possible example and it may be needless to say that the capacity is by no means limited to the above cited value. Similarly, the timing of inspection and that of deviation handling in a deviation handling apparatus 1 according to the present invention may appropriately be determined according to the specifications of the system and they are by no means limited to the above cited related numerical values. Additionally, the shutoff valves 35 and 36 and the switching valve 49 may not necessarily be pneumatically driven and electrically driven valves may alternatively be employed.

The present invention is applicable not only to systems for continuously manufacturing granulated products to be used for tablets but also to systems for manufacturing granulated products to be used for foods and fertilizers.

What is claimed is:

1. A deviation handling apparatus to be used for a continuous production system of granulated products used for pharmaceutical products, foods and fertilizers in order to discharge granulated products not meeting predetermined product specifications out of the system, the deviation handling apparatus comprising:
   a storage section for temporarily storing granulated products;
   an inspection section for inspecting selected physical properties of the granulated products in the storage section;
   a discharge path arranged downstream relative to the storage section to discharge the granulated products to outside of the continuous production system; and a switching section for switching a moving route of the granulated products according to a result of the inspection by the inspection section so as to guide the granulated products judged as not meeting the predetermined product specifications to the discharge path, wherein the storage section is arranged on a conveyance route for conveying the granulated products in the continuous production system and has a first valve capable of shutting off the conveyance route, a second valve capable of shutting off the conveyance route, the second valve being located downstream relative to the first valve, and a storage chamber formed between the first valve and the second valve to store the granulated products, the first valve and the second valve each have a closed position for shutting off the conveyance route and an open position for opening the conveyance route, wherein as the first valve and the second valve are placed into the respective closed positions, the conveyance route is closed and the storage chamber is sealed, thereby producing a hermetically sealed storage chamber in the storage section, the inspection section is arranged so as to face the storage chamber and measure the selected physical properties of the granulated products stored in the storage chamber, and the switching section is arranged at a diverging portion of the discharge path and the conveyance route and has a switching valve having a first position for causing the conveyance route to communicate with a downstream side of the continuous production system and a second position for closing a downstream side of the conveyance route and causing the conveyance route to communicate with the discharge path.

2. The deviation handling apparatus according to claim 1, further comprising:

a granulation apparatus that is configured to perform a wet granulation step for continuously forming wet granulated products and a drying apparatus that is configured to perform a drying step and arranged downstream relative to the granulation apparatus to dry the wet granulated products.

3. The deviation handling apparatus according to claim 1, wherein the deviation handling apparatus is arranged on a vertically extending part of the conveyance route for conveying the granulated products in the continuous production system.

4. The deviation handling apparatus according to claim 1, wherein the inspection section measures at least one of a particle size distribution, an average particle size, an amount of moisture, and a content of a specific ingredient as the selected physical properties of the granulated products.

5. A deviation handling method to be used for a continuous production system of granulated products used for pharmaceutical products, foods and fertilizers in order to discharge the granulated products not meeting predetermined specifications from the continuous production system, the deviation handling method comprising:

on a conveyance route for conveying the granulated products in the continuous production system, placing a first valve that is capable of shutting off the conveyance route, placing a second valve that is capable of shutting off the conveyance route, the second valve being located downstream relative to the first valve, and placing a storage chamber between the first valve and the second valve for storing of the granulated products;

sealing the storage chamber, by the shutting off of the conveyance route by closing the first valve and closing the second valve, so as to produce a hermetically sealed storage chamber;

once the second valve is shut off by the closing of the second valve, blocking a flow of the granulated products through the conveyance route and temporarily storing the granulated products in the storage chamber as the first valve is shut off by the closing of the first valve;

inspecting selected physical properties of the granulated products stored in the temporarily storing of the granulated products in the storage chamber; and judging, based on a result of the inspecting, whether one or more than one of the granulated products do not meet the predetermined specifications, and when the one or the more than one of the granulated products are judged in the judging as not meeting the predetermined specifications, discharging all the granulated products in the storage chamber to outside of the continuous production system, wherein the discharging is by way of a discharge path that is arranged downstream relative to the storage chamber in order to discharge the granulated products to the outside of the continuous production system, and the deviation handling method further comprises:

arranging a switching valve downstream relative to the storage chamber, the switching valve having a first position for causing the conveyance route to communicate with a downstream side of the continuous production system and a second position for shutting off a downstream side of the conveyance route and causing the conveyance route to communicate with the discharge path; and when the granulated products in the storage chamber are judged in the judging as not meeting the predetermined specifications, switching the switching valve to the second position to discharge the granulated product to the outside of the continuous production system.

* * * * *